United States Patent
Olivo et al.

(10) Patent No.: US 6,270,958 B1
(45) Date of Patent: Aug. 7, 2001

(54) DETECTION OF NEGATIVE-STRAND RNA VIRUSES

(75) Inventors: Paul D. Olivo; Sondra Schlesinger, both of St. Louis, MO (US); Mark E. Peeples, Berwyn, IL (US); Peter Collins, Rockville, MD (US)

(73) Assignees: Washington University, St. Louis, MO (US); National Institute of Health, Bethesda, MD (US); Rush Presbyterian St. Luke's Medical Center, Chicago, IL (US)

( * ) Notice: Subject to any disclaimer, the term of this patent is extended or adjusted under 35 U.S.C. 154(b) by 0 days.

(21) Appl. No.: 09/253,445

(22) Filed: Feb. 19, 1999

Related U.S. Application Data
(60) Provisional application No. 60/106,175, filed on Oct. 29, 1998.

(51) Int. Cl.⁷ ............................... C12Q 1/70; C12N 5/10

(52) U.S. Cl. .................... 435/5; 435/30; 435/34; 435/325; 435/810; 435/975

(58) Field of Search ............................ 435/325, 235.1, 435/5, 810, 30, 34, 975

(56) References Cited

U.S. PATENT DOCUMENTS
| | | |
|---|---|---|
| 5,418,132 | 5/1995 | Olivo . |
| 5,591,579 | 1/1997 | Olivo et al. . |

OTHER PUBLICATIONS

Muhlberger et al. Journal of virology 72 (11) p8756–64 (Abstract only), Nov. 1998.*
Welzel et al. Virus genes 17 (2) p185–98 (Abstract only), 1998.*
Johnson et al. Journal of virology 71 (4) p3323–7 (Abstract only), Apr. 1997.*
Penzes et al. Advances in experimental medicine and biology 440 p319–25 (Abstract only), 1998.*
Richt et al. Emerging infectious diseases (United States) Jul.–Sep. 1997, 3 (3)P343–52, 1997.*
Olivo et al., Detection and Quantitation of Human Respiratory Syncytial Virus (RSV) Using Minigenome cDNA and a Sindbis Virus Replicon: A Prototype Assay for Negative–Strand RNA Viruses, *Virology* 251, 198–205 (1998).
Agapov et al., Noncytopathic Sindbus virus RNA vectors for heterologous gene expression, *Proc. Natl. Acad. Sci. USA* 95:12989–12994 (1998).
Atreya et al., The NS1 Protein of Human Repiratory Syncytial Virus Is a Potent Inhibitor of Minigenome Transcription and RNA Replication, *J. Virol.* 72(2):1452–1461 (1998).
Bukreyev et al., Recovery of Infectious Respiratory Syncytial Virus Expressing an Additional, Foreign Gene, *J. Virol.* 70:6634–6641 (1996).
Collins et al., Rescue of synthetic analogs of respiratory syncytial virus genomic RNA and effect of truncations and mutations on the expression of a foreign reporter gene, *Proc. Natl. Acad. Sci. USA* 88:9663–9667 (1991).
Collins et al., Production of infectious human respiratory syncytial virus from cloned cDNA confirms an essential role for the transcription elongation factor from the 5' proximal open reading frame of the M2 mRNA in gene expression and provides a capability for vaccine development, *Proc. Natl. Acad. Sci. USA* 92:11563–11567 (1995).
Collins et al., Transcription elongation factor of respiratory syncytial virus, a nonsegmented negative–strand RNA virus, *Proc. Natl. Acad. Sci. USA* 93:81–85 (1996).
Conzelmann et al., Rescue of Synthetic Genomic RNA Analogs of Rabies Virus by Plasmid–Encoded Proteins, *J. Virol.* 68:713–719 (1994).
De et al., Rescue of Synthetic Analogs of Genome RNA of Human Parainfluenza Virus Type 3, *Virol.* 196:344–348 (1993).
Dimock et al., Rescue of Synthetic Analogs of Genomic RNA and Replicative–Intermediate RNA of Human Parainfluenza Virus Type 3, *J. Virol.* 67:27722–2778 (1993).
Frolov et al., Alphavirus–based expression vectors: Strategies and applications, *Proc. natl. Acad. sci USA* 93:11371–11377 (1996).
Garcia–Sastre et al., Genetic Manipulation of Negative–Strand RNA Virus Genomes, *Annu. Rev. Microbiol.* 47:765–790 (1993).
Garcin et al., A highly recombinogenic system for the recovery of infectious Sendai paramyxovirus from cDNA: generation of a novel copy–back nondefective interfering virus, *EMBO J.* 14:6087–6094 (1995).
Grosfeld et al., RNA Replication by Respiratory Syncytial Virus (RSV) Is Directed by the N, P, and L Proteins; Transcription Also Occurs under These Conditions but Requires RSV Superinfection for Efficient Synthesis of Full–Length mRNA, *J. of Virol.* 69:5677–5686 (1995).
Lawson et al., Recombinant vesicular stomatitis viruses from DNA, *Proc. Natl. Acad. Sci. USA* 92:4477–4481 (1995).
Lindenbach et al., trans–Complementation of Yellow Fever Virus NS1 Reveals a Role in Early RNA Replication, *J. Virol.* 71:9608–9617 (1997).

(List continued on next page.)

*Primary Examiner*—Mary E. Mosher
(74) *Attorney, Agent, or Firm*—Howell & Haferkamp, L.C.

(57) ABSTRACT

A diagnostic assay for detecting a negative-strand RNA virus in a sample and a genetically engineered cell for use in the assay are disclosed. The cell expresses a heterologous DNA-dependent RNA polymerase that synthesizes a minigenome or miniantigenome of the RNA virus from a cDNA template present in the cell. The cell also expresses the nucleocapsid proteins of the negative-strand virus that are necessary for replication of the minigenome or miniantigenome. Infection of the cell by the negative-strand virus results in expression of a reporter gene product encoded by the miniantigenome.

21 Claims, 11 Drawing Sheets

OTHER PUBLICATIONS

Olivo, Transgenic Cell Lines for Detection of Animal Viruses, *Clin. Microb Rev.* 9:321–334 (1996).

Radecke et al., Rescue of measles viruses from cloned DNA, *EMBO J.* 14:5773–5784 (1995).

Schnell et al., Infectious rabies viruses from cloned cDNA, *EMBO J.* 13:4195–4203 (1994).

Whelan et al., Efficient recovery of infectious vesicular stomatitis virus entirely from cDNA clones, *Proc. Natl. Acad. Sci. USA* 92:8388–8392 (1995).

Yu et al., Functional cDNA Clones of the Human Respiratory Syncytial (RS) Virus N, P, and L Proteins Support Replication of RS Virus Genomic RNA Analogs and Define Minimal trans–Acting Requirements for RNA Replication, *J. Virol.* 69:2412–2419 (1995).

* cited by examiner

DETECTION OF NEGATIVE-STRAND RNA VIRUSES

This application claims the benefit of U.S. Provisional Application No. 60/106,175 filed Oct. 29, 1998.

REFERENCE TO GOVERNMENT SUPPORT

This invention was made with U.S. Government support under Grant No. AI11377 awarded by the National Institutes of Health. The U.S. Government has certain rights in the invention.

BACKGROUND OF THE INVENTION (1) Field of the Invention

This invention generally relates to the field of virology and, more particularly, to a method for detecting a negative-strand RNA virus in a biological specimen and genetically engineered cells for use in the method.

(2) Description of Related Art

Numerous negative-strand RNA viruses are pathogenic to humans and other animals. Examples of human diseases caused by negative-strand viruses include mumps, measles, pneumonia, bronchitis, influenza, infectious croup, rabies, ebola hemorrhagic fever, marburg hemorrhagic fever, and LaCrosse encephalitis. Thus, detection of negative-strand viruses in biological specimens is important clinically and for various research purposes.

Although there is considerable diversity in the genomic structure and biological properties of negative-strand RNA viruses, the RNA replication and transcription strategies of these viruses have common features. As with all RNA viruses, negative-strand RNA viruses express an RNA-dependent RNA polymerase and other RNA replicase and transcriptase factors necessary to transcribe their mRNA and replicate their genomes (Olivo, P. D., *Clin. Microb. Rev.* 9:321–334, 1996). In the virion of a negative-strand virus, the RNA polymerase forms a complex with the nucleocapsid protein and the genomic RNA. Once the virion enters the cell and begins to uncoat, the virion RNA polymerase transcribes subgenomic mRNAs from the genomic RNA. The RNA polymerase also synthesizes full-length positive-strand replicative-intermediate RNA (antigenome), which is used as a template for making many copies of negative-stranded genomic RNA that then are used as templates for secondary transcription of additional viral mRNAs.

The study of negative-strand viruses has been complicated by the fact that the RNA-dependent RNA polymerase uses as template only RNA associated with virus-specific nucleocapsid proteins; thus, naked genomic RNA transfected into a cell is not replicated (Bukreyev et al., *J. Virol.* 70:6634–6641, 1996; Olivo, supra). Recently, however, a number of laboratories have described advances in the genetic manipulation of various negative-strand RNA viruses. For example, infectious rabies virus, Sendai virus, vesicular stomatitis virus, measles virus, and respiratory syncytial virus (RSV) have been reportedly recovered by using T7 RNA polymerase to generate a full-length antigenomic transcript from a cDNA of the genome in the cell cytoplasm together with the viral proteins necessary for assembly of a nucleocapsid and for RNA replication and transcription (Schnell et al., *EMBO J* 13:4195–4203, 1994; Garcin et al., *EMBO J* 14:6087–6094, 1995; Lawson et al., *Proc. Natl. Acad. Sci. USA* 92:4477–4481, 1995; Radecke et al., *EMBO J* 14:5773–5784, 1995; Whelan et al., *Proc. Natl. Acad. Sci. USA* 92:8388–8392, 1995; Collins et al., *Proc. Natl. Acad. Sci. USA* 92:11563–11567, 1995). In these reports, the T7 RNA polymerase was provided to the cell cytoplasm by infection with a recombinant vaccinia virus containing the gene for T7 RNA polymerase.

Other studies investigating viral protein function in replication and transcription of negative-strand RNA viruses have employed "minigenomes", in which some or all of the viral protein-coding sequences are replaced with a reporter gene flanked by cis-acting elements necessary for replication and transcription. See, e.g., Grosfeld et al., *J. of Virol.* 69:5677–5686, 1995; Conzelmann et al., *J. Virol.* 68:713–719, 1994; De et al., *Virol.* 196:344–348, 1993; Dimock et al., *J. Virol.* 67:27722–2778, 1993. In this approach, a cDNA is constructed in which the minigenome is operably linked to a promoter for a bacteriophage RNA polymerase, and the minigenome cDNA is transfected into cells and transcribed by the bacteriophage RNA polymerase in the presence of various viral proteins supplied by cotransfected plasmids, whose expression is also driven by the bacteriophage RNA polymerase, which is supplied by infection with a recombinant vaccinia virus. Induction of reporter gene expression indicates the transfected cell is expressing all the viral proteins needed to replicate and transcribe the minigenome.

Using this approach to study replication and transcription in RSV, the major nucleocapsid protein (N), the nucleocapsid-associated phosphoprotein (P), and the polymerase L protein were identified as sufficient to replicate the minigenome (Grosfeld et al., supra; Yu et al., *J. Virol.* 69:2412–2419, 1995). Coexpression of the N, P, and L proteins with a minigenome containing the cat reporter gene also resulted in synthesis of full-size and incomplete CAT mRNA species and abundant expression of CAT (Grosfeld et al., supra). In contrast, efficient synthesis of full-length mRNA was observed when cells containing the minigenome cDNA and the N, P and L expression plasmids were coinfected with the T7-expressing vaccinia virus and RSV, i.e., the minigenome RNA and the N, P and L proteins were synthesized by T7 RNA polymerase in the presence of infectious RSV (Grosfeld et al., supra). A later study demonstrated that expression of an additional RSV protein, the transcription elongation factor M2-1, was required for fully processive sequential transcription in this T7-expression plasmid complementation system (Collins et al., *Proc. Natl. Acad. Sci. USA* 93:81–85, 1996).

In U.S. Pat. No. 5,591,579, a genetically engineered cell line and method for detecting positive-strand RNA viruses was described. The cell line is stably transformed with a cDNA copy of a structurally defective RNA virus genome which contains (1) the cis-acting sequences of the RNA virus genome which are necessary for replication and transcription by trans-acting enzymes from the RNA virus and (2) a reporter gene. The cDNA is constitutively transcribed into a (+) strand RNA molecule from a RNA polymerase II promoter in the nucleus of the host cell, but little or no expression of the reporter gene occurs until the cell is infected by a positive-strand RNA virus that recognizes the cis-acting sequences and causes significant replication of the (+) strand RNA molecule through a (−) strand RNA intermediate.

Recently, a review article on the use of transgenic cell lines for detecting animal viruses speculated that a similar strategy could be used to make a cell line for detecting negative-strand RNA viruses (Olivo et al., supra). The article stated generally that such a cell line would constitutively express the viral nucleocapsid protein and a chimeric antigenomic RNA molecule which contains a reporter gene open reading frame (ORF) and the cis-acting sequences necessary for replication and transcription by the replicase and transcriptase of the same negative-strand RNA virus. This chimeric RNA molecule would be designed, in an unspecified manner, to preclude translation of the reporter gene in uninfected cells. Replication and transcription of the chimeric RNA molecule and synthesis of translatable reporter gene mRNA would be carried out by the replicase-transcriptase complex brought into this hypothetical cell by infection with the negative-strand RNA virus. However, this article did not teach how the nucleocapsid protein and chimeric RNA molecule would be constitutively expressed or how to design the chimeric RNA molecule to preclude translation of the reporter gene in the absence of infectious virus. It would be desirable, therefore, to provide a rapid, specific, sensitive and cost-efficient assay for the detection of infectious negative-stranded RNA viruses.

SUMMARY OF THE INVENTION

Briefly, therefore, the present invention is directed to novel compositions and methods which permit the detection of a negative-strand RNA virus in a specimen. In one embodiment, the invention provides a genetically engineered cell which expresses a reporter gene product only in the presence of infectious virions of the negative-strand RNA virus. The genetically engineered cell comprises a polynucleotide encoding a DNA-dependent RNA polymerase and a cDNA comprising a minigenome and a miniantigenome of the negative-strand RNA virus operably linked to a promoter for the DNA-dependent RNA polymerase. The miniantigenome comprises a nucleotide sequence encoding a reporter gene product whose expression is dependent upon the presence of the negative-strand RNA virus.

Expression of the DNA-dependent RNA polymerase in the cell results in transcription of the cDNA into a minigenome RNA or an miniantigenome RNA, depending on the orientation of the promoter with respect to the open reading frame (ORF) of the reporter gene. When the promoter is located downstream of the ORF, a minigenome RNA is synthesized which contains an untranslatable negative-sense copy of the reporter gene ORF and when the promoter is located upstream of the ORF, a miniantigenome RNA is synthesized. Although this miniantigenome contains a positive-sense copy of the reporter gene ORF, its translation is very inefficient because the miniantigenome is not a capped, polyadenylated mRNA. Thus, detectable expression of the reporter gene in the absence of infectious virus does not occur.

The cell also comprises one or more nucleotide sequences encoding each of the nucleocapsid proteins of the negative-strand RNA virus which are necessary and sufficient for replication of the minigenome RNA or miniantigenome RNA synthesized by the DNA-dependent RNA polymerase. Minigenome RNA synthesized in the presence of these nucleocapsid proteins, which includes minigenome RNA made as an intermediate during replication of the miniantigenome, is stabilized and amplified without detectable expression of the reporter gene product. Infection of the cell with the negative-strand virus introduces all the viral gene products necessary for transcription of the preformed minigenome RNA to produce translatable mRNA molecules encoding the reporter gene product.

In another embodiment, the invention provides a method for detecting a negative-strand RNA virus in a sample which comprises culturing the above-described genetically engineered cell for a time sufficient to synthesize the minigenome or miniantigenome RNA and the nucleocapsid proteins, then incubating the cells with the sample and detecting expression of the reporter gene product. In some embodiments, the method includes quantifying the number of infectious particles of the RNA virus that are present in the sample.

In other embodiments the genetically engineered cell is used to screen compounds for anti-viral activity and for measuring antibody responses of individuals infected with or vaccinated against the RNA virus.

In yet another embodiment, the invention provides a kit for detecting the presence of a negative-strand RNA virus in a sample which comprises a supply of the above-described genetically engineered cells. In a preferred embodiment, the kit also includes a set of reagents for detecting expression of the reporter gene product.

The invention also provides a method for making a genetically-engineered cell capable of detecting a negative-strand RNA virus. The method comprises (1) providing a cell that is susceptible to infection by the negative-strand RNA virus; (2) introducing into the cell a polynucleotide encoding a DNA-dependent RNA polymerase and selecting for cells containing the polynucleotide; (3) introducing into the selected cells a cDNA comprising a minigenome and an miniantigenome of the negative-strand RNA virus operably linked to a promoter for the DNA-dependent RNA polymerase, wherein the miniantigenome comprises a nucleotide sequence encoding a reporter gene product, and wherein expression of the reporter gene product is dependent upon the presence of the negative-strand RNA virus; and (3) introducing into the cells one or more nucleotide sequences encoding each of the nucleocapsid proteins of the negative-strand RNA virus which are necessary and sufficient for replication of minigenome RNA or miniantigenome RNA synthesized by the DNA-dependent RNA polymerase.

Among the several advantages of the present invention may be noted the provision of a genetically engineered cell which expresses a reporter gene product only after infection by a particular negative-strand RNA virus; the provision of a rapid and sensitive assay for specifically detecting the negative-strand RNA virus; the provision of such an assay that is capable of quantitating the amount of the negative-strand RNA virus in a sample that can be useful for assessing compounds for antiviral activity and for measuring antibody responses in infected or vaccinated individuals; and the provision of a kit for detecting and/or quantitating the negative-strand RNA virus.

DESCRIPTION OF PREFERRED EMBODIMENTS

Figure 1A:
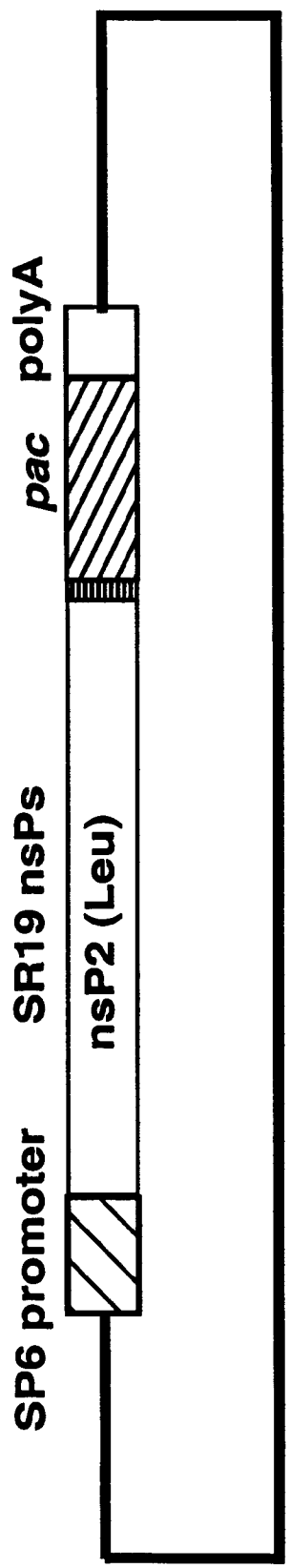
FIG. 1A is a schematic representation of SR19/pac cDNA, showing an SP6 promoter operably linked to a DNA copy of a noncytopathic Sindbis virus replicon in which the gene for puromycin acetyltransferase (PAC) is operably linked to the Sindbis subgenomic promoter.

In accordance with the present invention, a method for detecting negative-strand RNA viruses and genetically engineered cells for use in the method are provided. The invention is based on the inventors' discoveries (1) that minigenome RNA of a negative-strand virus expressed by a genetically engineered cell in the presence of certain viral nucleocapsid proteins is accessible for transcription of translatable reporter gene mRNA when the cell is subsequently infected with the negative-strand virus and (2) that expression of the product of the reporter gene is not detectably expressed in the absence of the negative-strand virus.

In the context of this disclosure, the following terms shall be defined as follows unless otherwise indicated:

"cis-acting sequences" means the nucleotide sequences from an RNA virus genome that are necessary for the recognition of the genomic RNA by specific protein(s) of the RNA virus that carry out replication and/or transcription of the genome;

"heterologous DNA-dependent RNA polymerase" means a DNA-dependent RNA polymerase not naturally encoded in a vertebrate cell;

"infectious" when used to describe a virus or an RNA molecule, means a virus or RNA molecule that is self-replicating and provides for transcription of viral mRNAs in a host cell;

"miniantigenome" means an RNA molecule or a DNA molecule that is complementary to a minigenome;

"minigenome" means a DNA or RNA analog of the genome of a negative-strand RNA virus which contains the cis-acting sequences necessary for replication and transcription in cells infected with the negative-strand RNA virus and which contains a negative-sense open reading frame of a reporter gene in place of one or more of the viral protein-coding sequences;

"negative-strand RNA virus" means a virus whose genome consists of one negative-sense RNA molecule (nonsegmented genome) or a plurality of RNA molecules of negative sense (segmented genome) and which replicates its genome through a positive-sense RNA intermediate(s);

"replicon" means a replication-competent viral RNA that contains the genetic information needed for virus replication but not for virus assembly;

"transfected cell" or "transformed cell" means a cell containing an exogenously introduced nucleic acid molecule which may be present in the nucleus or the cytoplasm of the cell;

"stably transformed cell" means a cell containing an exogenously introduced nucleic acid molecule which is present in the nucleus of the cell and may be stably integrated into the chromosomal DNA of the cell.

A genetically engineered cell according to the present invention is a vertebrate cell that is susceptible to infection by the negative-strand RNA virus to be detected and that is capable of expressing a heterologous DNA-dependent RNA polymerase which synthesizes a minigenome RNA or miniantigenome RNA of a negative-strand virus from a promoter recognized by the DNA-dependent RNA polymerase. The cell is also capable of expressing the nucleocapsid proteins of the negative-strand virus that are necessary for replication of the minigenome RNA or miniantigenome RNA.

A cell is susceptible to infection if the infecting virus can enter the cell and proceed far enough in its replication cycle to express proteins necessary for efficient synthesis of translatable reporter gene mRNA from preformed minigenome RNA. It will be understood by those skilled in the art that cell lines susceptible to infection by a particular negative-strand RNA virus can be readily identified by searching the literature for known susceptible cell lines and/or by screening candidate cell lines using well-known procedures requiring only routine experimentation. Susceptible cells for negative-strand RNA viruses include, but are not limited to baby hamster kidney cells, African green monkey cells, rabbit skin fibroblasts, 3T3 mouse cells and the like. Baby hamster kidney cells are preferred for use as the host cell for detecting negative-strand viruses that infect mammals, including humans.

The heterologous DNA-dependent RNA polymerase expressed by the cell comprises a naturally-occurring amino acid sequence or a functional equivalent thereof. A functional equivalent of a DNA-dependent RNA polymerase contains one or more amino acid substitutions, additions or deletions in the naturally-occurring amino acid sequence that do not prevent the modified polymerase from synthesizing full-length transcripts from a DNA template. Typically, the heterologous DNA-dependent RNA polymerase comprises the amino acid sequence of an RNA polymerase made by a bacteriophage such as T7, T3 or SP6. A preferred DNA-dependent RNA polymerase for use in the present invention is T7 RNA polymerase.

In one embodiment, the heterologous DNA-dependent RNA polymerase is encoded by a polynucleotide integrated into the cell nucleus and comprises a polymerase II promoter recognized by the host cell transcription machinery operably linked to a nucleotide sequence encoding the heterologous DNA-dependent RNA polymerase. In a preferred embodiment, the polynucleotide encoding the heterologous DNA-dependent RNA polymerase is an RNA molecule that comprises a noncytopathic positive-strand virus replicon. Use of a noncytopathic replicon allows for long-term, continuous expression of the DNA-dependent RNA polymerase without killing the host cell. Modification of replicons to make them noncytopathic is known in the art and can be accomplished, i.e., by isolating variants having adaptive mutations in the viral replication machinery that allows persistent noncytopathic replication in vertebrate cells or by using a dominant selectable marker (see e.g., Frolov et al., *Proc. Natl. Acad. Sci. USA* 93:11371–11377, 1996 and referenced cited therein). Preferred viruses for preparation of noncytopathic replicons include flaviviruses, e.g., Kunjin virus, alphaviruses such as Sindbis virus, Semliki forest virus, nodaviruses such as flock house virus, astroviruses and coronaviruses. The noncytopathic replicon can be transcribed from a cDNA of the replicon that is operably linked to a polymerase II promoter and integrated into the nucleus. Alternatively, the replicon can be prepared chemically or by in vitro transcription from a plasmid and then transfected into the cell cytoplasm.

The heterologous DNA-dependent RNA polymerase specifically recognizes a promoter in a cDNA comprising a minigenome and a miniantigenome of the negative-strand RNA virus to be detected. Typically, the nucleotide sequence of the promoter is identical to a promoter sequence found in the same organism that encodes the DNA-dependent RNA polymerase. However, the promoter may contain one or more nucleotide substitutions in the naturally-occurring sequence, as long as such substitutions do not affect specificity of recognition by the DNA-dependent RNA polymerase. The promoter is operably linked to either the DNA sequence encoding the minigenome or to the DNA sequence encoding the miniantigenome to direct the synthesis of either minigenome RNA or miniantigenome RNA, respectively. Preferably, the promoter directs the synthesis of minigenome RNA.

The minigenome encoded by the cDNA comprises the cis-acting 3'-leader and 5'-trailer sequences from the viral genome that are necessary for its replication and transcription by the viral-encoded RNA-dependent RNA polymerase. For the detection of RNA viruses having segmented genomes, it is believed that cis-acting sequences from any of the segments will make a functional minigenome. These cis-acting sequences flank a negative-sense copy of a reporter gene ORF, which is operably linked to gene-start (GS) and gene-end/polyadenylation (GE) transcription signals that are recognized by the RNA-dependent RNA polymerase. The leader, trailer, GS and GE sequences for any particular negative-strand RNA virus can be found in the scientific literature or can be identified by the skilled artisan using well-known and routine techniques. See, e.g., Weng et al., *Genome Res.* 5:202–207, 1995; Garcia-Sastre et al., *Annu. Rev. Microbiol.* 47:765–790, 1993 and references cited therein. In addition, it is intended that the minigenome can contain modifications in the naturally-occurring leader, trailer, GS and GE sequences that do not destroy replication or transcription of the minigenome or production of reporter gene mRNA in the presence of the negative-strand virus.

Any reporter gene that encodes a detectable product is suitable for use in the present invention. The reporter gene product is preferably one that can easily be assayed for or detected in a cell. One enzyme that has proved to be particularly useful as a reporter gene product is β-galactosidase. Preferably, a bacterial β-galactosidase is used, and most preferably the β-galactosidase from *E. coli* that is encoded by the LacZ gene. β-galactosidase is preferred because of its well-characterized nature and the existence of a variety of methods to detect its presence. Other reporter gene products useful in this invention generally include hydrolases or oxidoreductases and, in particular, such enzymes as β-glucosidase, β-glucuronidase, β-hexosaminidase, luciferase, phospholipase, phosphatase, etc. Green fluorescent protein (GFP) is another reporter gene product useful in the invention.

An ORF encoding β-galactosidase or luciferase is particularly preferred for use in this invention because of the numerous methods known to detect expression of these enzymes and the relative sensitivity of such methods. Among these methods include histochemical assays involving a chromogenic or fluorogenic substrate which permits detection of β-galactosidase activity by a change in the color of the cell that can be detected macroscopically or microscopically. The use of luciferase provides an enzymatic assay that is more sensitive than the colorimetric or fluorometric β-galactosidase assay. Expression of luciferase may be detected by known luminometric methods using luciferin as the enzyme substrate.

The minigenome or miniantigenome synthesized by the DNA-dependent RNA polymerase should have replication competent termini. These can be generated by appropriate construction of the minigenome-encoding cDNA using methods known in the art. For example, the cDNA can include at least one transcription terminator recognized by the DNA-dependent RNA polymerase in operable linkage with the minigenome or the miniantigenome. More preferably, the cDNA also comprises a self-cleaving ribozyme located between the transcription terminator and the 3'-terminus of the minigenome or miniantigenome. The position of the ribozyme is such that a transcript of the cDNA synthesized by the DNA-dependent RNA polymerase is cleaved by the ribozyme to produce a minigenome RNA or miniantigenome RNA having a replication competent 3'-terminus. Similarly, the cDNA can also contain a self-cleaving ribozyme positioned between the promoter for the DNA-dependent RNA polymerase and the trailer or leader sequence of the minigenome or miniantigenome, respectively, such that the 5'-terminus is replication competent. A number of self-cleaving ribozymes suitable for use in the invention are known in the art. See, e.g., Grosfeld et al., supra; Long et al., *FASEB J.* 7:25–30, 1993; Perrotta et al., *Nature* 350:434–436, 1991.

The genetically engineered cell also comprises one or more nucleotide sequences encoding the nucleocapsid proteins that are necessary and sufficient for replication of the minigenome RNA or miniantigenome RNA transcribed from the cDNA. As used herein, "necessary and sufficient for replication" is intended to mean that minigenome RNA or miniantigenome RNA synthesized from the cDNA in the presence of these nucleocapsid proteins is replicated in the absence of the negative-strand virus to be detected while detectable expression of the reporter gene product does not occur until the cell is infected with the negative-strand virus. As used herein, the terms "detectable expression of the reporter gene product" and "dependent upon the presence of the negative-strand virus" mean that the reporter gene product is practically detectable above background levels in the particular diagnostic assay being used, with background levels referring to measurements taken when the assay is performed in the absence of infectious virus or with genetically-engineered cells that lack the reporter gene.

As demonstrated below, the nucleocapsid proteins necessary and sufficient for replication of an RSV minigenome are the N, P and L proteins. Functional counterparts of these proteins in other negative-strand viruses can be identified from the scientific literature and by using methods known in the art. The combination of nucleocapsid proteins that are necessary and sufficient to replicate the minigenome of any particular negative-strand virus can be determined as described below in Example 3. In brief, T7-expression plasmids are constructed that express each of the nucleocapsid proteins and various combinations of these plasmids are introduced into a vertebrate cell expressing T7 RNA polymerase and containing a minigenome-encoding cDNA. The resulting genetically-engineered cell is incubated for a time sufficient for minigenome replication to proceed and then the cell is mock-infected or infected with the negative-strand virus and expression of the reporter gene product is measured. A combination of nucleocapsid proteins suitable for use in the present invention is one whose pre-infection expression results in cells that lack detectable reporter gene product in the absence of virus but that show efficient expression of the reporter gene product in the presence of the virus. It is intended that any or all of these nucleocapsid proteins may contain amino acid substitutions or deletions in the naturally-occurring sequence as long as the modified protein(s) functions in an equivalent manner as the native protein.

The nucleotide sequences encoding the desired nucleocapsid proteins can be provided by separate polynucleotides cotransfected into the cell or can be provided by a single polynucleotide in which separate transcription units encode the desired nucleocapsid proteins. Expression of mRNAs for the nucleocapsid proteins can be directed by promoters and transcription termination signals recognized by the heterologous DNA-dependent RNA polymerase expressed in the host cell cytoplasm or by polymerase II in the host cell nucleus. In embodiments in which a noncytopathic replicon expresses the DNA-dependent RNA polymerase, the replicon can also contain the nucleotide sequences encoding the nucleocapsid proteins arranged such that the replicon expresses mRNAs for each of the nucleocapsid proteins from a different subgenomic promoter. In a preferred embodiment, the heterologous DNA-dependent RNA polymerase is T7, T3, or SP6 RNA polymerase and the nucleotide sequences for the desired nucleocapsid proteins are operably linked to the corresponding T7, T3, or SP6 promoter.

In accordance with the method provided by the invention, the above-described genetically-engineered cells can be used to test a sample for the presence of a negative-strand virus. The sample can be any material which can be placed into a fluid or fluid environment and includes biological fluids such as blood, semen, nasopharyngeal swabs, cerebrospinal fluids and the like.

To carry out the method, the genetically engineered cells are first cultured for a period of time sufficient for synthesis of the minigenome or miniantigenome RNA and for expression of the nucleocapsid proteins. It is believed this culture step provides the minigenome RNA in an encapsidated form that is accessible for efficient expression of the reporter gene product by the replicase/transcriptase machinery of the incoming virus. Typically, this first culture period will be between 16 and 24 hours, but shorter or longer culture times may also produce functional, encapsidated minigenome RNA and the culture time suitable for a particular assay can be determined empirically.

The pre-cultured cells are then incubated with the sample in a suitable culture medium for a period of time sufficient for the infectious cycle of the target RNA virus to proceed. If the target virus is in the specimen, it will produce the factor(s) necessary for detectable expression of the reporter gene product. Typically, this incubation period is between 24 and 48 hours, although the optimal length for any particular negative-strand RNA virus should be determined empirically. Expression of the reporter gene product can be detected in the cells, in the culture medium, or in cell extracts.

The invention also provides a kit for detecting a negative-strand RNA virus. The kit is prepared by placing in a container a supply of the above-described genetically-engineered cells sufficient to conduct an assay or a number of assays in accordance with the invention. Preferably, the kit is also provided with reagents necessary for detecting the reporter gene product, placed in separate containers. An instruction manual can also be included in the kit.

The method and cells of this invention are useful for the detection of negative-strand RNA viruses belonging to the following families: Rhabdoviridae, Filoviridae, Paramyxoviridae, Orthomyxoviridae, Bunyaviridae, and Arenaviridae.

The following examples of the present invention are offered by way of illustration and are not to be considered in a limiting sense.

EXAMPLE 1

This example illustrates that T7 RNA polymerase expressed by a Sindbis virus replicon in baby hamster kidney (BHK) cells is functional.

As discussed above, studies of replication and transcription in negative-strand viruses have primarily used a vaccinia virus/T7 RNA polymerase system to supply intracellular T7 RNA polymerase for transcription of a desired gene under the control of the T7 promoter. However, an RNA detection method requiring coinfection with vaccinia virus would not be practicable for clinical diagnostic purposes. Thus, the inventors herein wished to develop a system that would permit the use of stably transformed cells, which would be easier to handle and allow more widespread use.

Recently, noncytopathic Sindbis virus replicons have been developed which contain the gene for puromycin resistance (pac) under control of the Sindbis subgenomic RNA promoter (SR19/pac) (Frolov et al., *Proc. Natl. Acad. Sci. USA* 93:11371–11377, 1996). Transfection of BHK cells with RNA transcribed in vitro from a cDNA of an SR19/pac replicon (FIG. 1A) produces a population of puromycin-resistant cells due to constitutive replication and transcription of the noncytopathic replicon and consequent expression of puromycin acetyl transferase. Modification of SR19/pac replicons to express an additional foreign gene operably linked to a second subgenomic RNA promoter has been achieved (Lindenbach et al., *J. Virol.* 71:9608–9617, 1997). For example, cells that carry a replicon expressing T7 RNA polymerase (SR19/T7Pol/pac) can transcribe a gene under the control of the T7 promoter following transfection of that gene (Agapov, E., et al., *Proc. Natl. Acad. Sci. USA* 95:12989–12994, 1998).

Figure 1B:
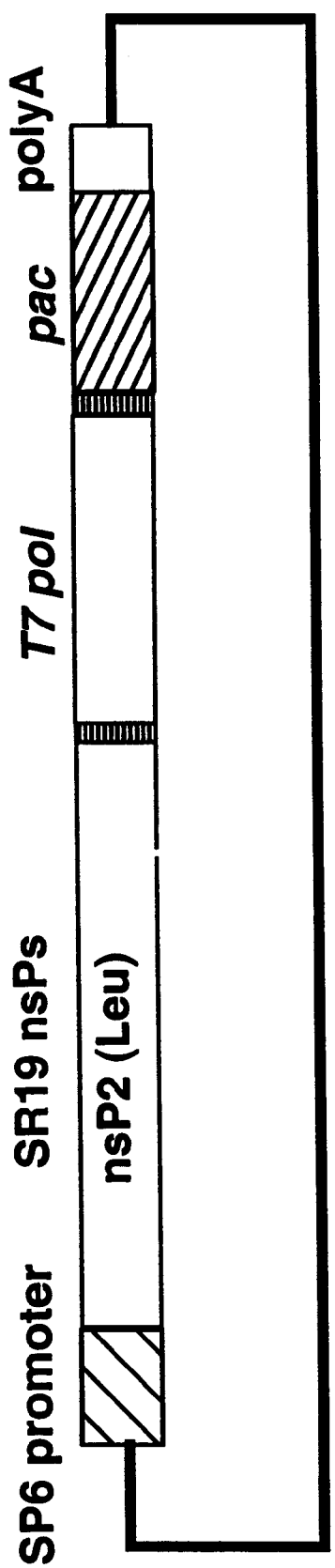
FIG. 1B is a schematic representation of SR19/T7pol/pac cDNA, which is identical to the cDNA of FIG. 1A except that the noncytopathic Sindbis virus replicon contains a the T7 RNA polymerase operably linked to a second Sindbis subgenomic promoter.

To determine if the SR19/T7pol/pac system could be used to express functional T7 RNA polymerase in BHK cells, replicon RNAs were transcribed in vitro from SR19/pac and SR19/T7Pol/pac cDNA plasmids (FIGS. 1A, 1B) (gift of Eugene Agapov and Charles Rice, Washington University School of Medicine, St. Louis, Mo.) using SP6 RNA polymerase. The replicon RNAs were electroporated into BHK-21 cells (ATCC) and replicon-containing cell populations were selected for puromycin resistance as described by Lindenbach et al., supra. The SR19/pac- and SR19/T7Pol/pac-transformed cells were then transfected with the T7 expression vector pTM1 (a generous gift of Bernard Moss, NIAID, Bethesda, Md.) or with pTM1-LacZ, which was generated by cloning the E. coli lacZ gene into the NcoI-BamHI window of the pTM-1 plasmid, thus placing the lacZ gene under control of the T7 promoter. The four groups of recombinant cells were maintained in puromycin-containing medium for 24 hours and then β-galactosidase activity in lysates prepared from these cells was determined as follows.

β-galactosidase activity was measured using the substrate chlorophenolred-β-D-galactopyranoside (CPRG, Boehringer Mannheim, Indianapolis, Ind.) (final concentration 5 mM) in a 0.2 M potassium phosphate buffer, pH 7.8, with 1 mM $MgCl_2$. Lysates were made in this buffer containing 1% Triton X-100 and 1 mM dithiothreitol. Fifty μliters of lysate were mixed with 50 μl of substrate in a microtiter plate well. After incubation for 30 to 120 min at room temperature, the optical density at a wavelength of 562 nM ($OD_{562}$) was measured with a THERMOmax microplate reader using SOFTmax software (Molecular Devices, Sunnyvale, Calif.). The assay was shown to be linear up to an $OD_{562}$ of 3.0.

Figure 2:
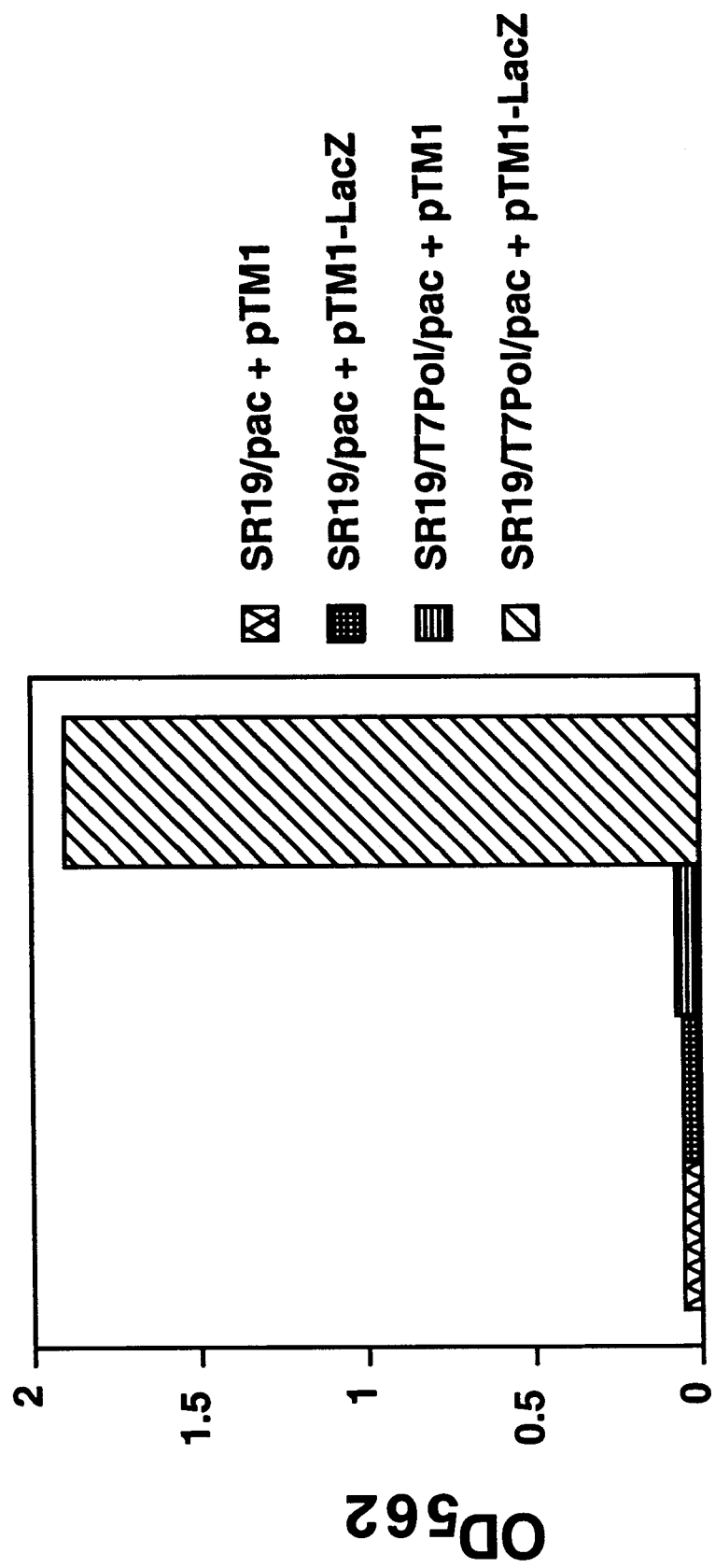
FIG. 2 is a bar graph of β-galactosidase activity in baby hamster kidney (BHK) cells transformed with a noncytopathic Sindbis virus replicon expressing T7 RNA polymerase (SR19/T7/pac) or the parent replicon (SR19/pac) and transfected with a T7 expression plasmid expressing the *E. coli* lacZ gene under the control of the T7 promoter (pTM1-LacZ) or the parent T7 expression plasmid (pTM1)

The amount of β-galactosidase activity in the four different groups of cells is shown in FIG. 2 (amounts shown are the mean of duplicate samples). High levels of β-galactosidase activity were detected in cells containing both the SR19/T7Pol/pac replicon and the pTM1-LacZ plasmid, but not in control cells that lacked the T7 RNA polymerase or the lacZ gene (FIG. 2). Thus, functional T7 RNA polymerase is expressed in BHK cells transfected with SR19/T7pol/pac RNA.

EXAMPLE 2

This example illustrates that SR19/T7Pol/pac-transformed BHK cells are susceptible to infection by the negative-strand virus RSV and that such RSV-infected cells support replication and transcription of an RSV minigenome.

SR19/T7Pol/pac BHK cells were mock-infected or infected with 10 plaque-forming units (pfu)/cell of RSV (strain A2), which was propogated and titered on HEp-2 cells as described previously (Grosfeld et al., supra). Forty-five minutes later, the cells were transfected over a 3-h period with 0.5–1.5 μg of in vitro-synthesized RSV-CAT minigenome RNA, which contains the bacterial cat gene in place of all of the viral protein open reading frames (Collins et al, Proc. Natl. Acad. Sci. USA 88:9663–9667, 1991). The minigenome RNA was a run-off transcript of 935 nt produced by T7 RNA polymerase of HgaI-linearized RSV-CAT cDNA (Collins et al., 1991). Only RSV-infected cells exhibited reporter gene expression (data not shown), indicating that SR19/T7Pol/pac BHK cells are permissive for RSV infection as well as RSV minigenome replication and expression.

The inventors next asked whether minigenome RNA transcribed in vivo in SR19/T7Pol/pac BHK cells was functional. SR19/T7Pol/pac BHK cells were mock-infected or infected with RSV (strain A2) at 10 plaque-forming units (pfu) per cell and 45 min. later were transfected with pC2CAT, a derivative of RSV-CAT cDNA which, inter alia, contains a hammerhead-type ribozyme sequence and T7 transcription terminator at the 3' end of the encoded transcript (Grosfeld et al., 1995, supra). Ribozyme self-cleavage of the T7-synthesized transcript of pC2CAT leaves a single non-RSV-specific 3'-phosphorylated U residue on the 3' terminus (Grosfeld et al., 1995, supra). Under these conditions, RSV-infected cells exhibited a marked increase in CAT activity as compared to CAT activity in mock-infected cells (data not shown).

The results of these experiments indicate that RSV-infected SR19/T7Pol/pac cells can produce a functional RSV minigenome from minigenome RNA or minigenome cDNA that is subsequently transfected into the cell.

EXAMPLE 3

This example illustrates that preformed minigenome RNA requires RSV nucleocapsid proteins for activity after RSV infection.

The assay initially envisioned by the inventors for detecting RSV in cell culture involved constitutive expression of an RSV minigenome RNA that would be replicated and transcribed after subsequent infection with RSV. To test the feasibility of this protocol, the following experiment was performed.

SR19/T7Pol/pac cells were transfected with pMP210, a cDNA of an RSV minigenome containing a negative-sense copy of the gene for green fluorescent protein (GFP), and 6–24 h later the cells were infected with 10 pfu of RSV. pMP210 was made from pC2Luc cDNA, which contains the luciferase gene substituted for the CAT gene in the above-described pC2CAT construct (Collins et al., Proc. Natl. Acad. Sci. USA 93:81–85, 1996). A PCR product containing the Green Lantern Protein gene (Life Technologies, Gaithesburg, Md.) flanked by gene start (GS) and gene end (GE) signals was inserted into the BstXI site in the leader of pC2Luc, and the luciferase gene was deleted. In addition, a 5' hammerhead ribozyme preceded by a unique AvrII site (Altschuler et al., Gene 122:85–90, 1992) was inserted just before the trailer sequence. The pC2 3' hammerhead ribozyme was replaced with a PCR product containing the antigenomic hepatitis delta virus ribozyme (Perrotta et al., Nature 350:434–436, 1991) followed by a unique XhoI site.

Under these conditions, no RSV-dependent GFP expression was observed. These negative results suggest that minigenome RNA has a very short half-life in uninfected BHK cells or is in some manner not accessible to or recognized by the incoming RSV replicase and/or transcriptase. Thus, a viable assay for detecting RSV infection using an RSV minigenome requires a strategy for stabilizing the minigenome RNA and/or making it replication competent.

It has been shown that RSV N, P, and L proteins are necessary and sufficient for replication of RSV minigenomes and that expression of the N, P, and L proteins leads to transcription of RSV mRNA, although not necessarily full-length mRNA (Grosfeld et al., supra; Yu et al., supra. In addition, expression of only the N and P proteins leads to encapsidation of RNA minigenomes and this is increased 10 to 50-fold by the addition of the L protein (Atreya et al., J. Virol. 72:1452–1461, 1998). Based on these results, the inventors investigated whether a minigenome expressed in the presence of the N, P, and L proteins would be accessible to transcription of reporter gene mRNA when the cells were subsequently infected with RSV.

Figure 3A:
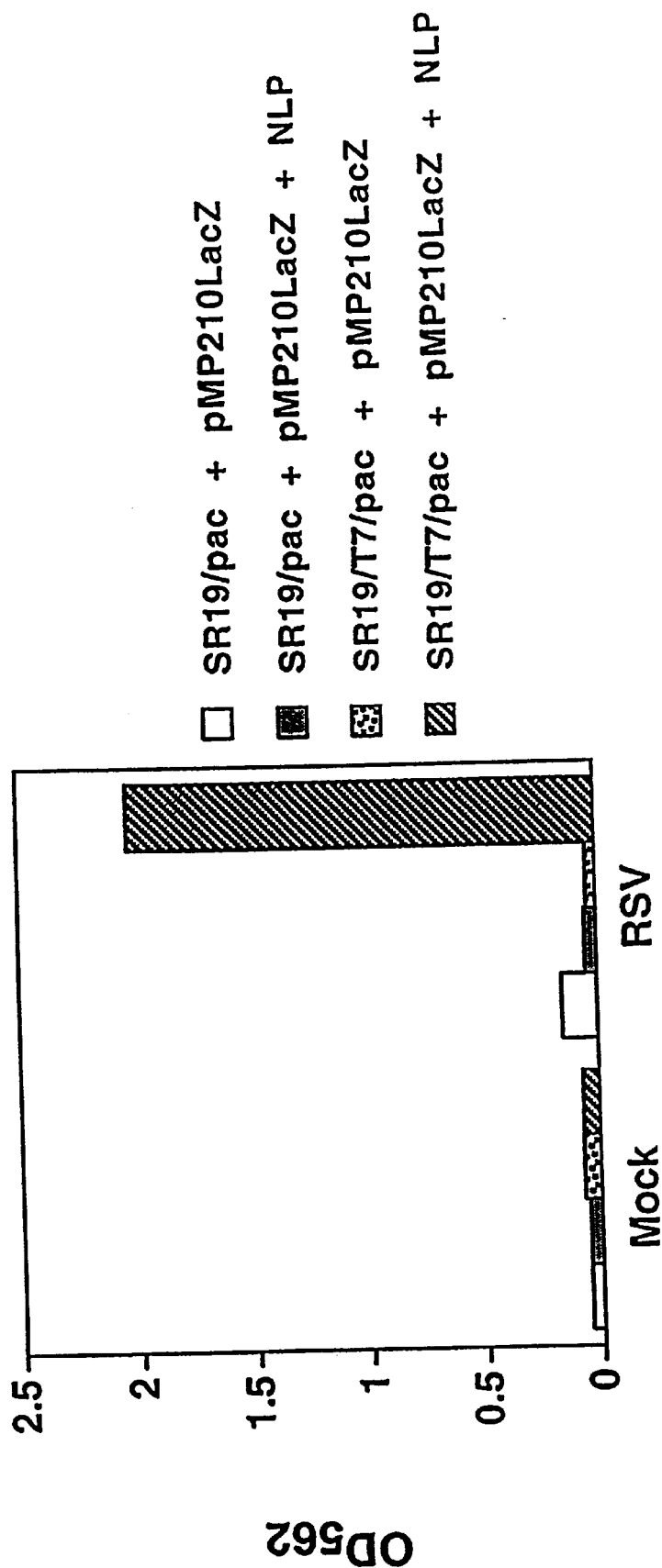
FIG. 3A is a bar graph of β-galactosidase activity in mock-infected or RSV-infected SR19/T7/pac-BHK or SR19/pac-BHK cells transfected with a cDNA of a lacz-containing RSV minigenome (pMP210LacZ) alone or with T7 expression plasmids expressing the RSV nucleocapsid proteins N, L and P (+NLP)

SR19/T7Pol/pac cells or SR19/pac cells were transfected with 1 μg of pMP210LacZ, a lacZ-containing minigenome cDNA, with or without 0.2 μg each of the T7 expression plasmids pTM1-N, pTM1-P,and pTM1-L described in Grosfeld et al., supra. pMP210LacZ was made by replacing the ORF of GFP in pMP210 with the ORF of lacZ using the unique XbaI and XmaI sites. Twenty hours after transfection the cells were trypsinized and plated in 24 well dishes and six hours later infected with RSV (5 pfu/cell) or mock-infected. At 36 hrs after infection, the cells were lysed and assayed for β-galactosidase as described above. The results, which are the mean of duplicate samples, are shown in FIG. 3A.

Figure 7:
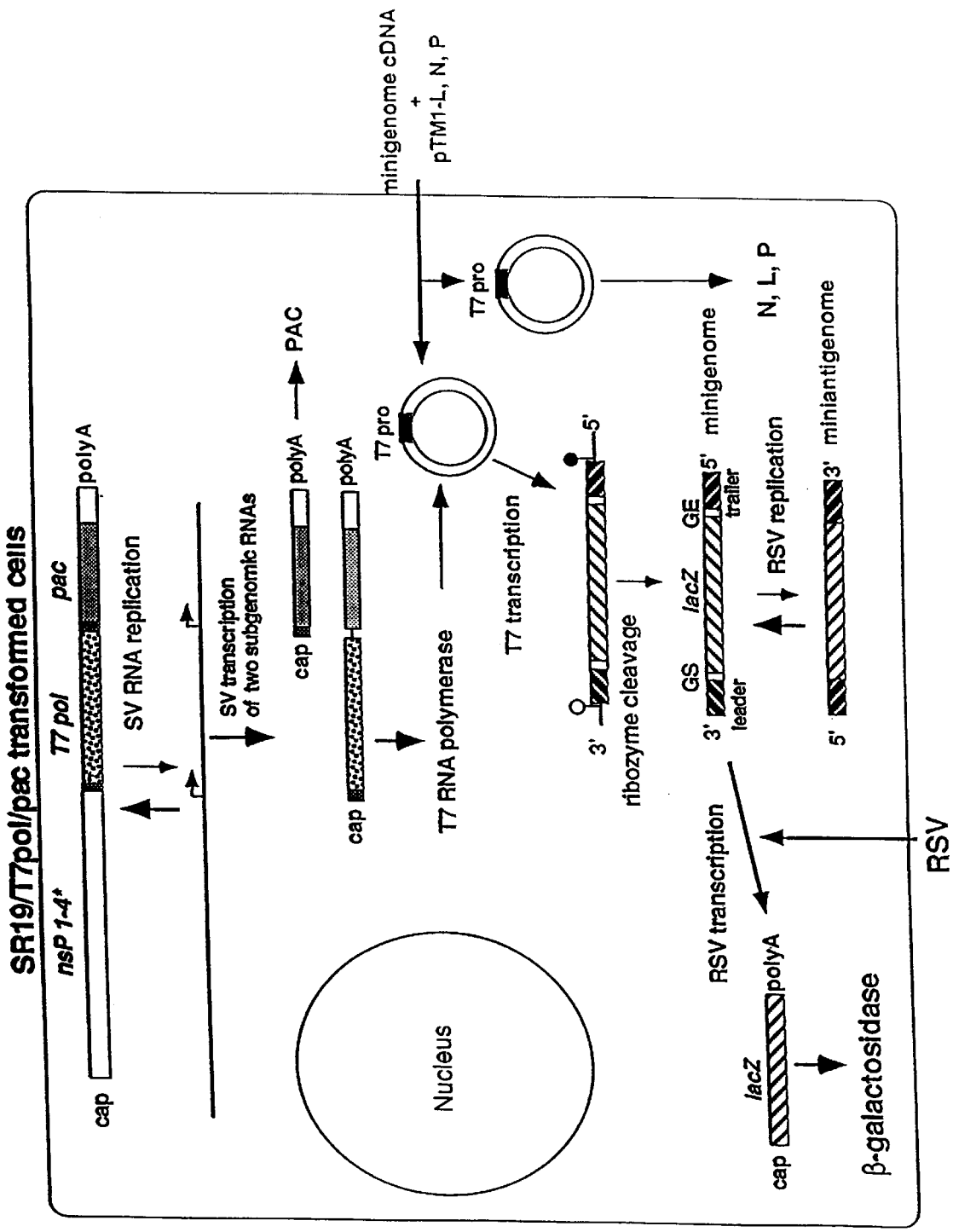
FIG. 7 is a schematic representation of the recombinant constructs and molecular pathways involved in generating a reporter gene product in accordance with one embodiment of the invention.

Significant induction of β-galactosidase activity by RSV infection was observed in cells expressing both T7 RNA polymerase and the RSV nucleocapsid proteins N, L and P. These cells are illustrated in FIG. 7. Notably, β-galactosidase activity in the corresponding mock-infected cells was not significantly higher than β-galactosidase activity in mock-infected cells lacking T7 (background) or in mock-infected cells lacking N, L and P.

Figure 3B:
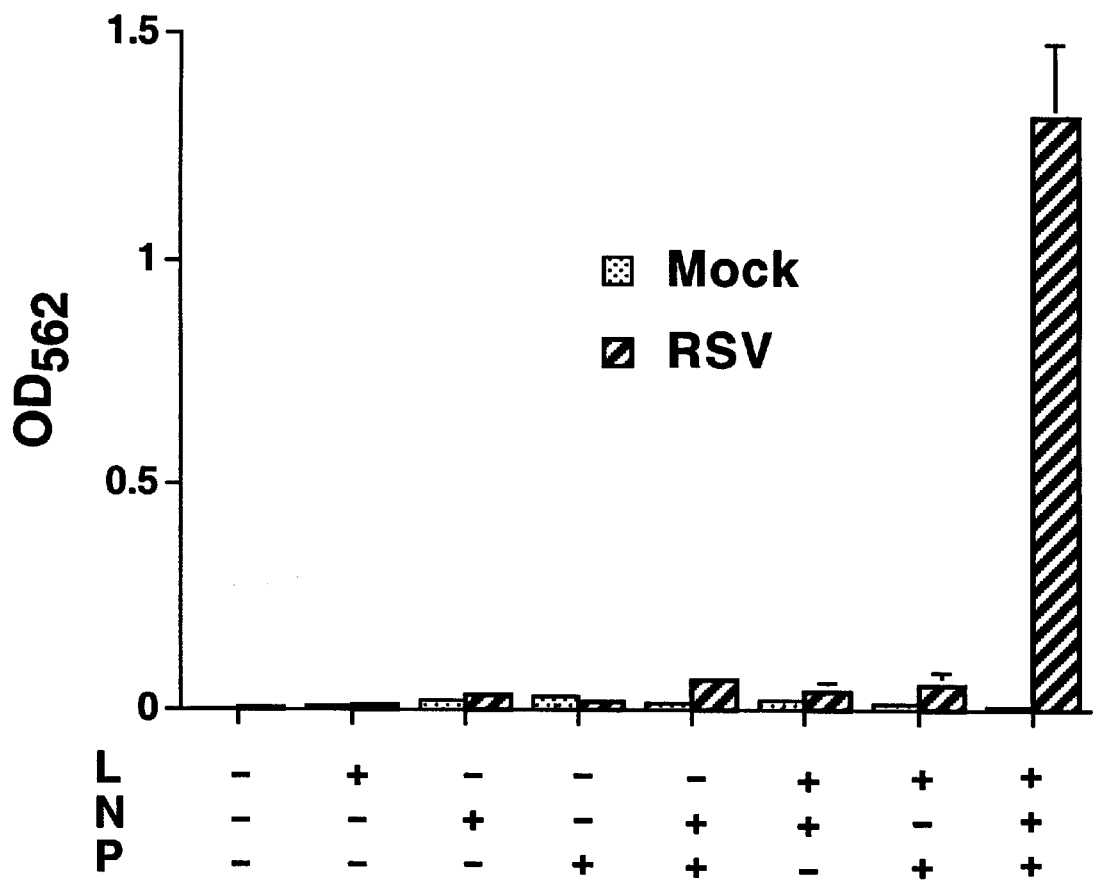
FIG. 3B is a bar graph of β-galactosidase activity in mock-infected or RSV-infected SR19/T7/pac-BHK or SR19/pac-BHK cells transfected with pMP210LacZ alone or with various combinations of the T7 expression plasmids for N, L and P as indicated by the + and − symbols below the graph.

To assess the relative requirement for each of the nucleocapsid proteins, various combinations of the N, L and P expression plasmids (0.2 μg each) were cotransfected with the minigenome cDNA (pMP210LacZ at 1 μg) into SR19/T7Pol/pac cells and the assay was carried out as above. The results, which are the mean of triplicate samples ± the standard deviation, are shown in FIG. 3B. RSV-induced β-galactosidase activity was significant only in the presence of all three nucleocapsid proteins. In addition, the amount of activity was unchanged when the assay was carried out after 10 passages of these minigenome-expressing cells.

When evaluated by histochemical staining as described in U.S. Pat. No. 5,418,132, β-galactosidase-positive infected cells were observed only in the presence of the nucleocapsid proteins: a few stained infected cells per well were observed with N alone or with N plus P, while many stained infected cells were consistently observed when N, P, and L were all expressed (data not shown). Significantly, no stained cells were observed in the absence of RSV with or without the nucleocapsid proteins. The requirement for all three nucleocapsid proteins in this assay suggests that encapsidation and replication of the minigenome RNA are necessary for efficient reporter gene expression by the incoming RSV. In addition, the lack of β-galactosidase activity in mock-infected cells expressing all three nucleocapsid proteins indicates that detectable expression of β-galactosidase is dependent upon some factor(s) provided by RSV infection, probably the M2-1 protein.

EXAMPLE 4

This example illustrates that the level of expression of the minigenome reporter gene is dependent on the input concentration of RSV.

Approximately $2 \times 10^6$ SR19/T7Pol/pac cells in six 9.5 cm² wells were transfected with pMP210LacZ (1 μg) and pTM 1-N, P, and L (0.2 μg each). After 18 h the transfected cells were trypsinized, pooled and plated into all the wells of a 48-well plate. Six h later approximately $10^5$ cells were either (A) infected with increasing volumes of a two-fold dilution of a stock RSV (titer $2 \times 10^7$ pfu/ml assayed on HEp2 cells) and β-galactosidase activity assayed 36 hr later or (B) infected with either 0.5 microliters (low multiplicity of infection; LMOI) or 25 microliters (high multiplicity of infection; HMOI) of the same stock virus and β-galactosidase activity assayed at the indicated times after infection. The results of the dose response assay are shown in FIG. 4A (expressed as the mean of triplicate samples ± the standard deviation) and the results of the time course assay are shown in FIG. 4B (the mean of duplicate samples).

Figure 4A:
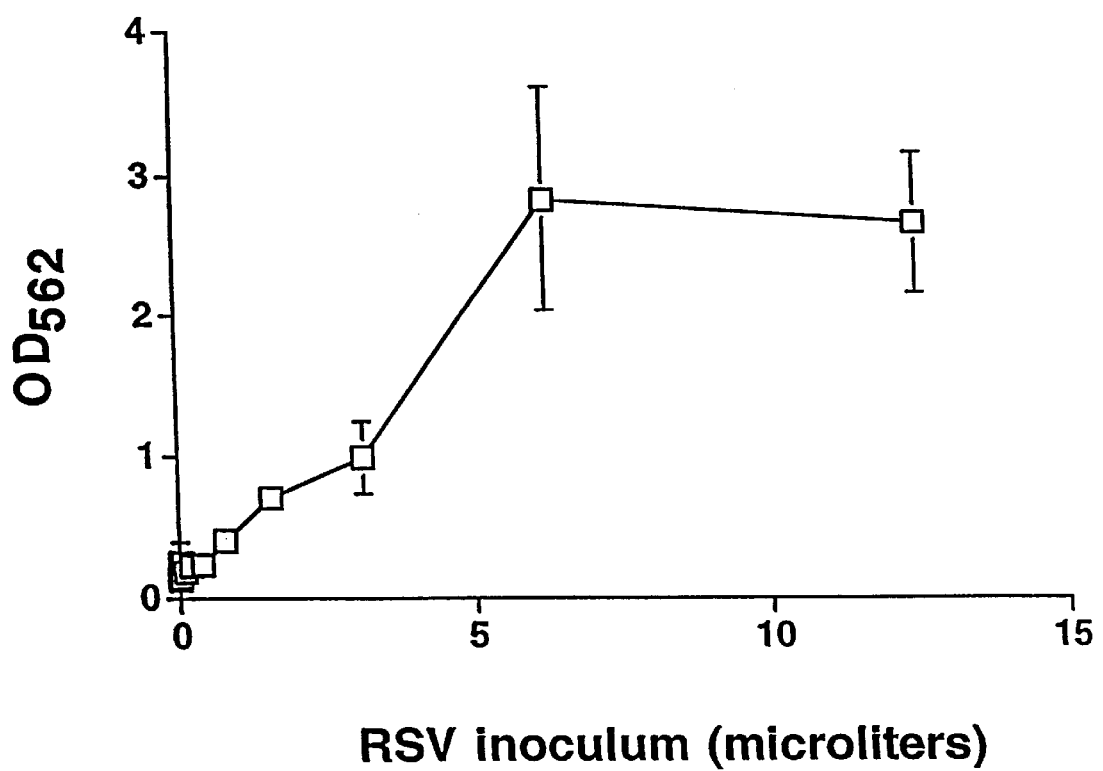
FIG. 4A is a graph of β-galactosidase activity in SR19/T7/pac-BHK cells cotransfected with pMP210LacZ and the nucleocapsid expression plasmids and infected with the indicated amounts of RSV.

The assay exhibited a relatively linear dose-response for RSV over a range of greater than one $\log_{10}$ (FIG. 4A). The RSV-induced expression exhibited a plateau effect above an inoculum equivalent to a multiplicity of infection of approximately 0.6 pfu/cell (based on HEp2 cells). These results indicate that this assay could be used in place of a plaque assay to quantitate RSV stocks.

Figure 4B:
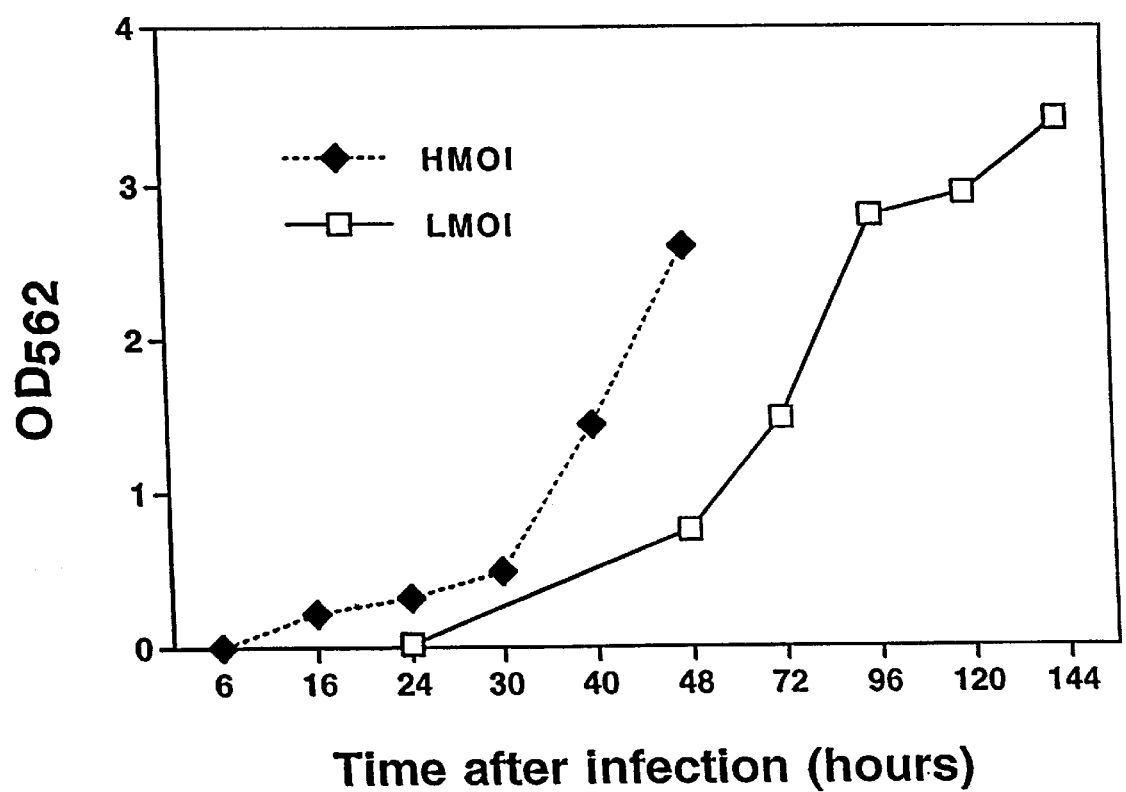
FIG. 4B is a graph of β-galactosidase activity in the cells from FIG. 4A at the indicated times following RSV infection at a high multiplicity of infection (HMIO) or at a low multiplicity of infection (LMOI)

When β-galactosidase in these minigenome-expressing cells was measured as a function of time after infection, β-galactosidase activity following a LMOI infection (0.2 pfu/cell) reached the same level as that following a HMOI infection (10 pfu/cell), but with a delay of approximately 48 h (FIG. 4B). This suggests that RSV replicates and spreads within these cell cultures and that the duration of an infectious cycle is approximately 48 h.

EXAMPLE 5

This example illustrates that RSV-induced expression of the minigenome reporter gene is sensitive to ribavirin.

Figure 5A:
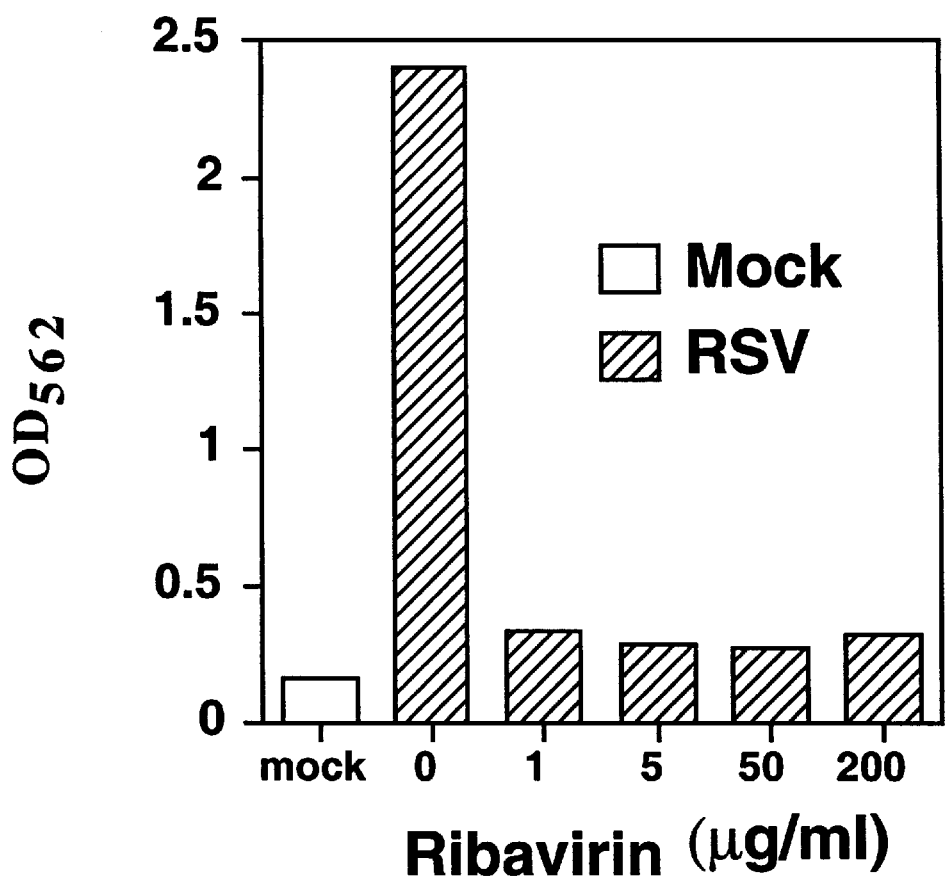
FIGS. 5A and 5B illustrate the effect of ribivarin on the induction of reporter gene activity in RSV-infected SR19/T7/pac-BHK cells cotransfected with pMP210LacZ and the nucleocapsid expression plasmids showing in FIG. 5A a bar graph of β-galactosidase activity at high concentrations of ribivarin and in FIG. 5B a dose-response curve of β-galactosidase activity at subinhibitory concentrations or ribivarin expressed as a percentage of the control.
Figure 5B:
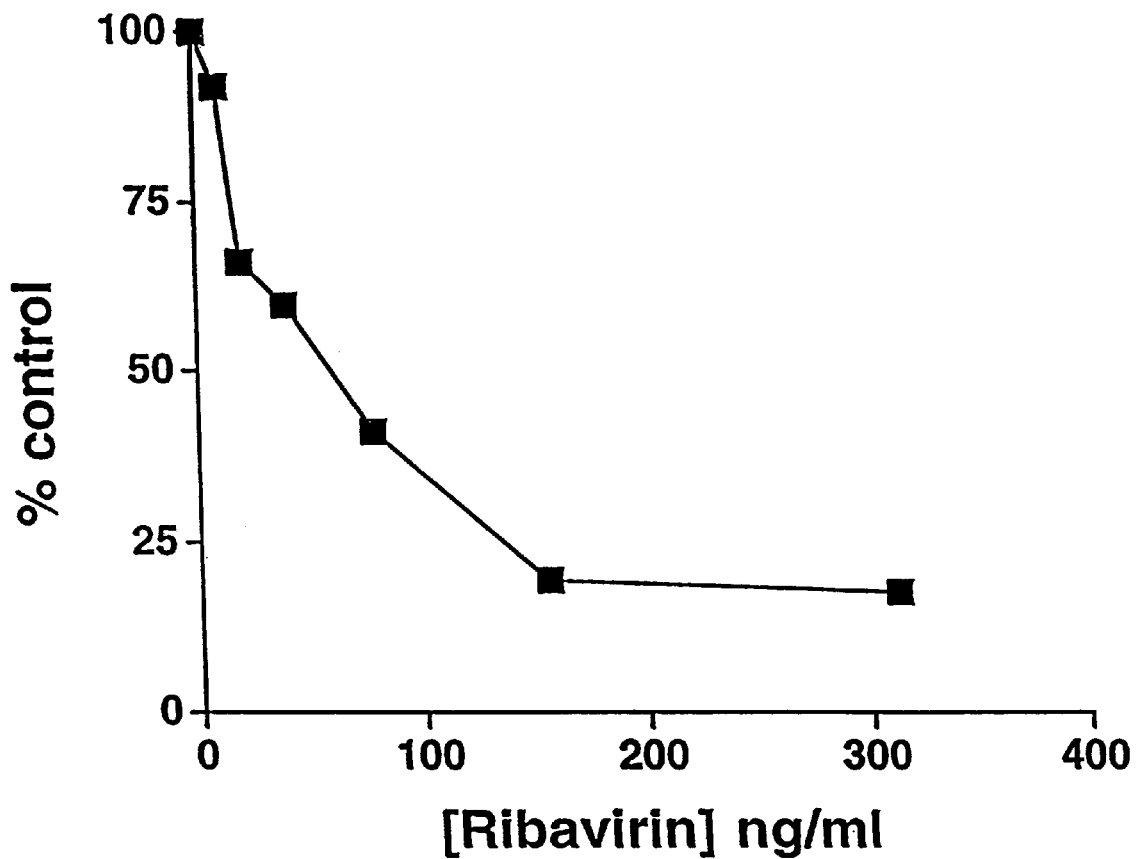

Ribavirin inhibits in vitro replication of many RNA viruses including RSV (Sidwell et al., *Pharmacol Ther* 6:123–146, 1979). Depending on the assay used, the 50% effective dose ($ED_{50}$) of ribavirin for RSV has been reported to be around 5 μg/ml (Chiba et al., *Biol Pharm Bull* 18:1081–1083, 1995). To determine if ribavirin affects the detection of RSV by a minigenome assay, SR19/T7Pol/pac cells were cotransfected with pMP210LacZ, pTM1-N, pTM1-P, and pTM1-L as described in Example 3 and then infected with RSV (5 pfu/cell) in the presence of 1, 5, 50 or 200 μg/ml of ribavirin. As shown in FIG. 5A, β-galactosidase activity was reduced to near background levels by as little as 1 μg/ml ribavirin (FIG. 5A). When this dose response experiment was repeated at subinhibitory concentrations between 0 and 400 ng/ml ribavirin, the $ED_{50}$ of ribavirin was determined to be less than 100 ng/ml (FIG. 5B).

Treatment of the cells with ribivarin (1 μg/ml) from the time of trnasfection of the RSV cDNA plasmids until the time of RSV infection had no effect on RSV-dependent β-galactosidase expression (data not shown). This suggests that under the conditions in which this assay was performed, ribavirin primarily affects RSV replication and transcription rather than the Sindbis replicon or T7 polymerase transcription and than any minigenome replication mediated by the RSV L protein occurring prior to replication of incoming RSV must be relatively insensitive to ribavirin.

EXAMPLE 6

This example illustrates that RSV-induced β-galactosidase activity in minigenome-expressing cells is sensitive to neutralizing antibody to RSV.

Figure 6:
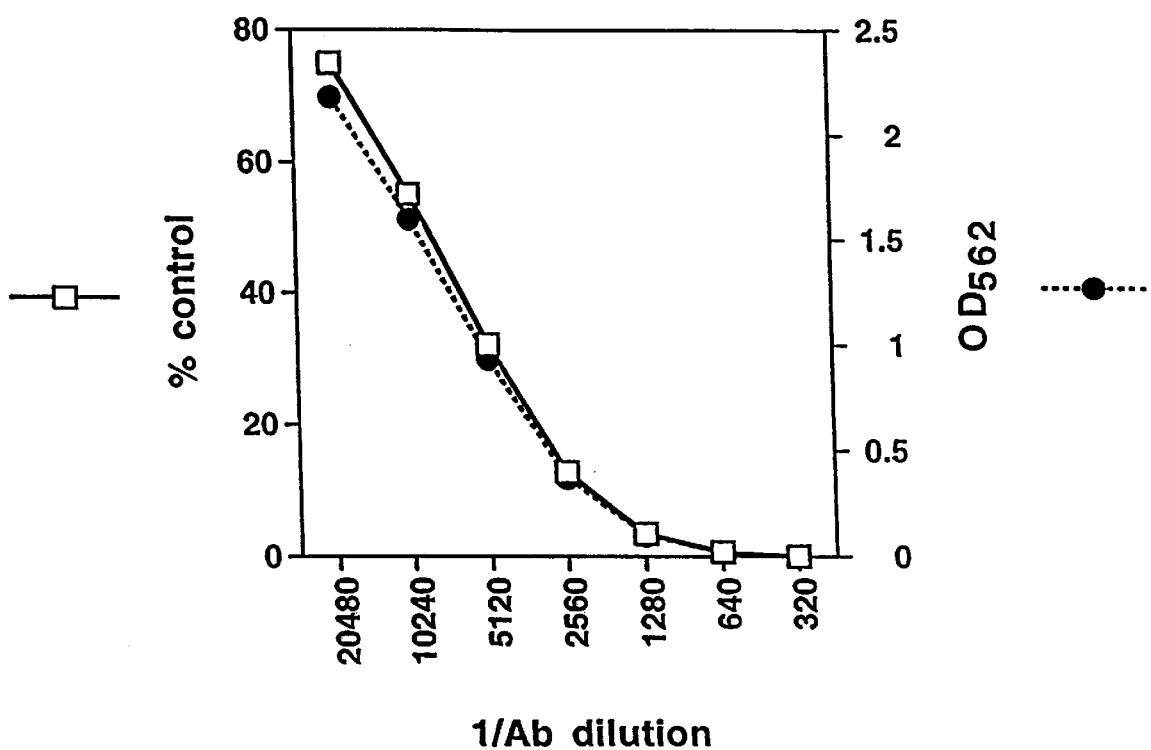
FIG. 6 is a graph of β-galactosidase activity in SR19/T7/pac-BHK cells cotransfected with pMP210LacZ and the nucleocapsid expression plasmids after infection with RSV which had been preincubated with the indicated dilutions of pooled human immune globulin.

To demonstrate that the RSV-induced β-galactosidase activity in this system requires infectious virus, and can, therefore, be blocked by neutralizing antibody, we incubated RSV with different dilutions of a sample of pooled human gamma globulin. RSV is a highly prevalent human pathogen and most adults have been infected at least once (Collins et al., Respiratory Syncytial Virus, pp. 1313–1350 in *Fields Virology*, B. N. Fields, D. M. Knipe and P. M. Howley, eds., Lippencott-Raven, Philadelphia, 1996). Therefore, pooled human gamma globulin has significant neutralizing activity against RSV. The globulin-treated virus was used to infect SR19/T7Pol/pac cells that had previously been transfected with pMP210LacZ and pTM1-N, pTM1-P, and pTM1-L. As shown in FIG. 6, β-galactosidase activity was inversely proportional to the amount of dilution of the gamma globulin sample.

EXAMPLE 7

This example illustrates the specificity of RSV minigenome-expressing cells in detecting RSV in patient samples.

SR19/T7Pol/pac cells that had previously been transfected with pMP210LacZ and pTM1-N, pTM1-P, and pTM1-L were incubated with two patient specimens, previously determined to contain RSV, or with patient specimens known to contain influenza A, influenza B, and parainfluenza types 1 and 2. Induction of β-galactosidase activity was determined by histochemical staining.

Incubation with the RSV-containing specimens produced significant β-galactosidase, while specimens containing the other negative-stranded viruses did not induce any positively stained cells (data not shown). Thus, the assay is specific for RSV.

The sensitivity of this assay can be enhanced by increasing the time of infection before assaying for β-galactosidase activity. At 36 h after infection, 3000 pfu could be detected; at 5 days after infection even an inoculum of less than 10 pfu gave a reading several-fold above background.

In view of the above, it will be seen that the several advantages of the invention are achieved and other advantageous results attained.

As various changes could be made in the above methods and compositions without departing from the scope of the invention, it is intended that all matter contained in the above description and shown in the accompanying drawings shall be interpreted as illustrative and not in a limiting sense.

All references cited in this specification, including patents and patent applications, are hereby incorporated by reference. The discussion of references herein is intended merely to summarize the assertions made by their authors and no admission is made that any reference constitutes prior art. Applicants reserve the right to challenge the accuracy and pertinency of the cited references.

What is claimed is:

1. A genetically engineered cell for detecting a negative-strand RNA virus, the cell comprising:
    a polynucleotide encoding a DNA-dependent RNA polymerase;
    a cDNA comprising a minigenome and a miniantigenome of the negative-strand RNA virus operably linked to a promoter for the DNA-dependent RNA polymerase, wherein the miniantigenome comprises a nucleotide sequence encoding a reporter gene product, and wherein expression of the reporter gene product is dependent upon the presence of the negative-strand RNA virus; and
    one or more nucleotide sequences encoding each of the nucleocapsid proteins of the negative-strand RNA virus which are necessary and sufficient for replication of minigenome RNA or miniantigenome RNA synthesized by the DNA-dependent RNA polymerase.

2. The genetically engineered cell of claim 1, wherein the DNA-dependent RNA polymerase is T7 RNA polymerase, T3 RNA polymerase or SP6 RNA polymerase.

3. The genetically engineered cell of claim 2, wherein the polynucleotide is integrated into the nucleus and comprises a polymerase II promoter operably linked to a nucleotide sequence encoding the DNA-dependent RNA polymerase.

4. The genetically engineered cell of claim 2, wherein the polynucleotide comprises a noncytopathic positive-strand virus replicon.

5. The genetically engineered cell of claim 4, wherein the noncytopathic positive-strand virus replicon comprises a noncytopathic flavivirus replicon, a noncytopathic alphavirus replicon, a noncytopathic nodavirus replicon, or a noncytopathic astrovirus replicon.

6. The genetically engineered cell of claim 5, wherein the negative-strand RNA virus is an orthomyxovirus, a paramyxovirus, a filovirus, or a bunyavirus.

7. The genetically engineered cell of claim 6, wherein the negative-strand RNA virus is selected from the group consisting of: human parainfluenza virus type 1, human parainfluenza virus type 2, human parainfluenza virus type 3, human parainfluenza virus type 4, human influenza virus, human respiratory syncytial virus (RSV), measles virus, mumps virus, rabies virus, Ebola virus and hanta virus.

8. The genetically cell of claim 7, wherein the reporter gene product is β-galactosidase, chloramphenicol acetyl transferase, luciferase, alkaline phosphatase, green fluorescent protein or β-glucuronidase.

9. The genetically engineered cell of claim 8, wherein the negative-strand RNA virus is RSV, the DNA-dependent RNA polymerase is T7 RNA polymerase, the reporter gene product is β-galactosidase, and the nucleocapsid proteins necessary and sufficient for replication of the minigenome are the RSV proteins N, P and L which are encoded by three T7 expression plasmids.

10. The genetically engineered cell of claim 7, wherein the reporter gene is β-galactosidase.

11. A method for detecting a negative-strand RNA virus in a sample, the method comprising:
    (a) providing a genetically engineered cell which comprises
        a polynucleotide encoding a DNA-dependent RNA polymerase;
        a cDNA comprising a minigenome and a miniantigenome of the negative-strand RNA virus operably linked to a promoter for the DNA-dependent RNA polymerase, wherein the miniantigenome comprises a nucleotide sequence encoding a reporter gene product, and wherein expression of the reporter gene product is dependent upon the presence of the negative-strand RNA virus; and
        one or more nucleotide sequences encoding each of the nucleocapsid proteins of the negative-strand RNA virus which are necessary and sufficient for replication of minigenome RNA or miniantigenome RNA synthesized by the DNA-dependent RNA polymerase;
    (b) culturing the cell for a time sufficient to synthesize the minigenome RNA or the miniantigenome RNA and to express the nucleocapsid proteins;
    (c) incubating the cell with the sample; and
    (d) detecting expression of the reporter gene product.

12. The method of claim 11, wherein the DNA-dependent RNA polymerase is T7 RNA polymerase, T3 RNA polymerase or SP6 RNA polymerase.

13. The method of claim 12, wherein the polynucleotide is integrated into the nucleus and comprises a polymerase II promoter capable of causing transcription of the polynucleotide.

14. The method of claim 12, wherein the polynucleotide comprises a transcript of a noncytopathic positive-strand virus replicon.

15. The method of claim 14, wherein the noncytopathic positive-strand virus replicon comprises a noncytopathic flavivirus replicon, a noncytopathic alphavirus replicon, a noncytopathic nodavirus replicon, or a noncytopathic astrovirus replicon.

16. The method of claim 15, wherein the negative-strand RNA virus is an orthomyxovirus, a paramyxovirus, a rhabdovirus, a filovirus, or a bunyavirus.

17. The method of claim 16, wherein the negative-strand RNA virus is selected from the group consisting of: human parainfluenza virus type 1, human parainfluenza virus type 2, human parainfluenza virus type 3, human parainfluenza virus type 4, human influenza virus, human respiratory syncytial virus (RSV), measles virus, mumps virus, rabies virus, ebola virus and hanta virus.

18. The method of claim 17, wherein the reporter gene product is β-galactosidase, chloramphenical acetyl transferase, luciferase, alkaline phosphatase, or green fluorescent protein.

19. The method of claim 18, wherein the negative-strand RNA virus is RSV, the DNA-dependent RNA polymerase is T7 RNA polymerase, the reporter gene product is β-galactosidase, and the nucleocapsid proteins necessary and sufficient for replication of the minigenome are the RSV proteins N, P and L which are encoded by three T7 expression plasmids.

20. A kit for detecting a negative-strand virus in a sample, the kit comprising:
 a container;
 said container containing a supply of genetically engineered cells which comprise:
  a polynucleotide encoding a DNA-dependent RNA polymerase;
  a cDNA comprising a minigenome and a miniantigenome of the negative-strand RNA virus operably linked to a promoter for the DNA-dependent RNA polymerase, wherein the miniantigenome comprises a nucleotide sequence encoding a reporter gene product, and wherein expression of he reporter gene product is dependent upon the presence of the negative-strand RNA virus; and,
 one or more nucleotide sequences encoding each of the nucleocapsid proteins of the negative-strand RNA virus which are necessary and sufficient for replication of minigenome RNA or miniantigenome RNA synthesized by the DNA-dependent RNA polymerase.

21. The kit of claim 20, further comprising a supply of reagents necessary to detect expression of the reporter gene product.

* * * * *